US006978656B2

(12) United States Patent
Blakley

(10) Patent No.: US 6,978,656 B2
(45) Date of Patent: Dec. 27, 2005

(54) TRANSDUCER-BASED SENSOR SYSTEM AND METHOD

(75) Inventor: Daniel R. Blakley, Philomath, OR (US)

(73) Assignee: Hewlett-Packard Development Company, L.P., Houston, TX (US)

(*) Notice: Subject to any disclaimer, the term of this patent is extended or adjusted under 35 U.S.C. 154(b) by 81 days.

(21) Appl. No.: 10/698,834

(22) Filed: Oct. 31, 2003

(65) Prior Publication Data

US 2005/0092088 A1 May 5, 2005

(51) Int. Cl.[7] .......................... G01N 29/02; H02N 2/04
(52) U.S. Cl. ................. 73/24.06; 73/24.01; 310/313 R
(58) Field of Search ...................... 73/572, 574, 24.01, 73/24.06, 24.03, 24.04, 24.05, 313 R, 313 A–313 D; 310/313 R, 313 A, 313 B, 313 C, 313 D

(56) References Cited

U.S. PATENT DOCUMENTS

| | | | |
|---|---|---|---|
| 3,582,838 A | 6/1971 | DeVries | |
| 3,983,424 A | 9/1976 | Parks | |
| 4,055,072 A | 10/1977 | Fletcher et al. | |
| 4,788,466 A | 11/1988 | Paul et al. | |
| 5,201,215 A | 4/1993 | Granstaff et al. | |
| 5,448,126 A | 9/1995 | Eda et al. | |
| 5,477,098 A | 12/1995 | Eguchi et al. | |
| 5,719,324 A * | 2/1998 | Thundat et al. | ............ 73/24.01 |
| 6,144,332 A | 11/2000 | Reindl et al. | |
| 6,167,748 B1 * | 1/2001 | Britton et al. | ............. 73/24.06 |
| 6,289,717 B1 * | 9/2001 | Thundat et al. | .............. 73/23.2 |
| 6,647,764 B1 * | 11/2003 | Paul et al. | ................. 73/54.41 |

(Continued)

FOREIGN PATENT DOCUMENTS

JP   55-40967   3/1980
WO   WO 01/02857   1/2001

OTHER PUBLICATIONS

"In Situ Interfacial Mass Detection With Piezoelectric Transducers", Michael D. Ward et al., Science, vol. 249, Issue 4972, Aug. 31, 1990, pp. 1000-1007.
"A Novel Immunosensor for Herpes Viruses", Bernd Konig et al., Analytical Chemistry, vol. 66, No. 3, Feb. 1, 1994, pp. 341-344.
"Piezoelectric Mass-Sensing Devices as Biosensors—An Alternative to Optical Biosensors?", Andreas Janshoff et al., The Quarz-Crystal Microbalance in Life Science, Amer. Chem. Int. Ed. 2000, 39, pp. 4004-4032.
"'Hearing' Bond Breakage, Measurement of Bond Rupture Forces Using a Quartz Crystal Microbalance", F. N. Dultsev et al., Langmuir 2000, 16, pp. 5036-5040.
"Listening for Viral Infection", Erica Ollmann Saphire et al., Nature Biotechnology, Sep. 2001, vol. 19, pp. 823-824.
"Direct and Sensitive Detection of a Human Virus by Rupture Event Scanning", Matthew A. Cooper et al., Nature Biotechnology, Sep. 2001, vol. 19, pp. 833-837.

Primary Examiner—Helen Kwok

(57) ABSTRACT

A system and method for performing rupture event scanning and other sensing operations on a sample. The method includes providing a transducer with an immobilized binding partner material and a sample material disposed thereon. The sample material is applied to the immobilized binding partner material so that, if components in the sample material have sufficient affinity for the immobilized binding partner material, bonds will form between at least some of such components and the immobilized binding partner material. The method further includes accelerating the transducer to induce bond breakage, where such accelerating is performed by applying a drive signal to the transducer. The drive signal includes a waveform having multiple frequency components that are pre-selected based on expected resonance behavior of the transducer. The method may also include analyzing an output response of the transducer in response to application of the drive signal.

41 Claims, 8 Drawing Sheets

U.S. PATENT DOCUMENTS 6,826,949 B1 * 12/2004 Berndt .................. 73/64.56
6,848,295 B2 * 2/2005 Auner et al. ............. 73/24.06
6,848,299 B2 * 2/2005 Paul et al. ............... 73/64.53
2002/0011761 A1 1/2002 Takeuchi et al.

* cited by examiner

TRANSDUCER-BASED SENSOR SYSTEM AND METHOD

BACKGROUND

Transducer devices are used in a variety of applications to transfer energy between electrical systems and mechanical systems. Quartz crystal microbalance (QCM), for example, is a transducer-based technology that may employ piezoelectric transducers in various configurations to perform sensing functions. QCM technology takes advantage of the fact that the resonant frequency of a transducer typically varies with the effective mass of the transducer. Accordingly, when portions of a sample material bind to the transducer, the mass of the bonded sample material can be detected by monitoring the resonant frequency of the vibrating mass.

A related technology is rupture event scanning (RES), in which transducers may be employed to produce mechanical energy to break bonds within a sample material. In addition to providing energy to break the bonds, the transducers may be used as sensors to analyze acoustic events (e.g., a pressure wave) that can occur when bonds break. Different types of bonds have unique properties that produce distinctive acoustic events. The bonds can be identified and analyzed by using various techniques to study the acoustic events.

Existing rupture event devices and methods typically employ high Q transducer devices which are excited with pure sinusoidal signals at the resonant frequency of the transducer. In existing devices and methods, continuous scanning operations are performed on the transducer to determine whether the system is still operating at resonance, and/or to determine whether a change in resonant frequency has occurred. This often requires use of a low-amplitude test signal to ensure that rupture events are not induced while the resonant frequency is being determined. In certain operational settings, the process of determining the resonant frequency, particularly when performed frequently and repeatedly, can significantly limit the speed at which samples are processed. Processing speed is also limited in many existing systems by the analytic methods used to study transducer output data.

SUMMARY

The present description provides a system and method for performing rupture event scanning and other sensing operations on a sample. The method includes providing a transducer with an immobilized binding partner material and a sample material disposed thereon. The sample material is applied to the immobilized binding partner material so that, if components in the sample material have sufficient affinity for the immobilized binding partner material, bonds will form between at least some of such components and the immobilized binding partner material. The method further includes accelerating the transducer to induce bond breakage, where such accelerating is performed by applying a drive signal to the transducer. The drive signal includes a waveform having multiple frequency components that are pre-selected based on expected resonance behavior of the transducer. The method may also include analyzing an output response of the transducer in response to application of the drive signal.

DETAILED DESCRIPTION

The following description relates to systems, devices and methods in which a transducer is employed to obtain information about materials secured to or in proximity with the transducer. For purposes of illustration only, the description will focus primarily on rupture event scanning (RES) and quartz crystal microbalance (QCM) applications.

Figure 1:
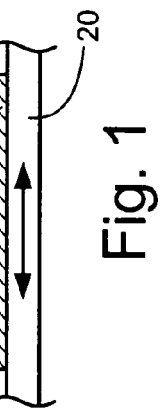
FIG. 1 is a depiction of an embodiment of an exemplary transducer according to the present description with a sample disposed thereon.

FIG. 1 depicts an exemplary transducer 20. Transducer 20 typically is a piezoelectric device formed from a quartz crystal or other material with piezoelectric properties. In RES, QCM and other applications, various materials may be provided on or around the transducer. Specifically, as shown in the figure, an immobilized binding partner material such as antibody sample 22 may be disposed on transducer 20. Transducer 20 may also be prepared with a sample material 24 including constituent components such as particles 26. If the components within the sample material have sufficient affinity for the immobilized binding partner material (e.g., for antibodies within the immobilized binding partner material), then bonds will form between the components and the immobilized binding partner. For example, if antibodies within antibody sample material 22 are exposed to complementary antigens (e.g., particles 26), the antibody-antigen pairs may form bonds.

Transducer 20 typically is coupled with a drive signal generator (not shown in FIG. 1) or like device for applying a drive signal to the transducer. Application of the drive signal typically creates a mechanical oscillation as indicated by the arrows in FIG. 1. An output processing system (not shown in the figure) may be employed to obtain and analyze electrical output resulting from movement of transducer 20. As the transducer oscillates in response to application of the drive signal, particles 26 experience an acceleration, and thus a force, that is proportional to the amplitude of the applied drive signal. When this force is equal to or greater than the energy or force associated with the bond (e.g., the bond between an antibody and antigen), the bond breaks. Breaking of the bond yields a unique acoustic signature that represents and is associated with the unique binding force(s) between the bonded components (e.g., between the particular antibody and antigen).

Applying a drive signal, such as a voltage waveform, typically will cause the transducer to move, due to the piezoelectric properties of the transducer. Often the movement of the transducer will be oscillatory in nature. In many cases it will be desirable to drive the transducer at its resonant frequency by driving it at its direct fundamental or direct overtone frequency in the frequency domain.

The resonant response of the transducer will be significant in many operational settings. For example, the resonant frequency of transducer 20 typically will vary with the effective mass of the transducer (e.g., the mass of the transducer itself and the mass of any material secured to the transducer). Specifically, resonant frequency increases as the effective transducer mass decreases. Accordingly, monitoring of frequency response (e.g., detection of resonant frequency changes) may be used in many applications to perform mass measurements. Referring specifically to FIG. 1, the effective mass of transducer 20 would be the mass of the transducer plus the mass of immobilized binding partner material 22 and the mass of any particles 26 secured or affixed to the binding partner material. By detecting changes in the resonant frequency, information may be obtained about particles 26 or other material dislodging from the surface of transducer 20. Specifically, the quantity of dislodged material may often be ascertained if the associated change in resonant frequency is known. If sample material 24 is known to contain only one type of particle 26 (e.g., a specific antigen), the number of particles involved in a rupture event may be determined, assuming that the mass of an individual particle 26 is known.

In addition to detecting mass dislodgment through variation in resonant frequency, specific information may be obtained about the bonds broken due to the oscillation of the transducer. As indicated above and explained in further detail below, bond breakage typically will produce an acoustic event. The acoustic event will in turn have a physical effect upon the transducer, that is, the acoustic event will cause a corresponding movement in the transducer, independent of and in addition to the movement caused by the applied drive signal. The transducer movement caused by the event will contribute components to the transducer's output, which may in turn be analyzed to obtain information about the occurrence producing the acoustic event. Such analysis may be employed, for example, to determine whether a sample material contains a specific type of particle 26, such as a specific antigen, pathogen, etc.

Figure 2:
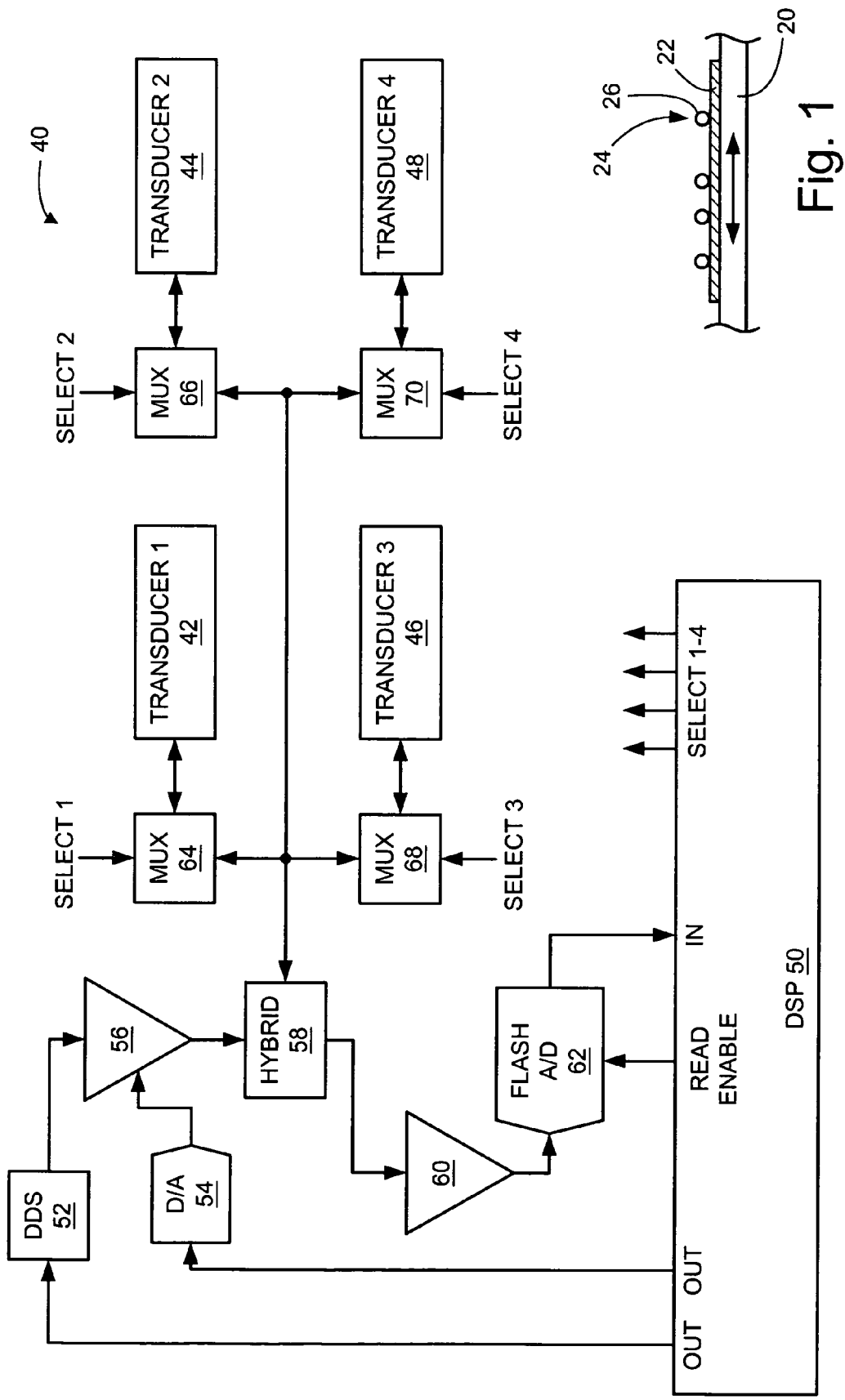
FIG. 2 is a schematic depiction of an embodiment of a transducer-based sensor system according to the present description, including multiple transducers and components for applying drive signals to the transducers and receiving output signals from the transducers.

FIG. 2 depicts a transducer system 40 that may be employed in RES, QCM and other applications involving transducers. System 40 typically includes an array of transducers similar to transducer 20, as opposed to a single transducer, to allow faster testing and/or testing of multiple samples. In the depicted example, system 40 includes four transducers 42, 44, 46 and 48, though it should be appreciated that any practicable number of transducers may be employed.

System 40 typically includes a controller, such as a processor and a memory coupled with the transducer array and configured to perform various functions. These functions may include performing overall system control, including sequential control of various system components; generating and applying drive signals to the transducer array in order to mechanically excite the transducers; controlling the energy imparted by the drive signals by controlling the amplitude and/or duration of the drive signals; detecting and/or obtaining resonant frequencies of the transducers, including initial frequencies and subsequent frequencies (e.g., after mass has been dislodged); sampling output from the transducers in response to application of the drive signals; storing the digitized output samples from the transducers; performing frequency domain transformations as appropriate on the sampled data; filtering or otherwise removing extraneous or unwanted portions of the sampled data; and comparing remaining portions of the sampled data to stored data, such as bond adhesion tables, to determine whether particular rupture events occurred. These functions will be described in more detail below. It should be understood that the recited functions are illustrative only, and should not be interpreted in a limiting or restrictive sense. The processor and memory may be implemented in a variety of ways and configured as desired to suit the needs of a particular application.

In the example of FIG. 2, the controller is implemented with a digital signal processor (DSP) 50 and various accompanying components, including a direct digital synthesizer (DDS) 52, digital-to-analog converter (DAC) 54, amplifier 56, hybrid RF device 58, amplifier 60 and a flash analog-to-digital converter (ADC) 62. A multiplexing device including sections 64, 66, 68 and 70 may also be provided to selectively activate desired transducers in the array.

During operation, DSP 50 and DDS 52 may be employed to generate an input voltage waveform (e.g., a drive signal) for application to one or more of transducers 42, 44, 46 and 48. The transducer or transducers are selected via multiplexer sections 64, 66, 68 and 70, which may be controlled via the depicted select lines 1–4 of DSP 50. The amplitude of the waveform may be controlled via operation of DAC 54 and amplifier 56, using values supplied from DSP 50. The resulting input drive signal may be applied to the selected transducer via RF hybrid device 58, which may be implemented as a four-port device in order to segregate input and output signals flowing in opposite directions to and from the array of transducers. Output signals flow through hybrid RF device 58, amplifier 60 and flash ADC 62. Outputs may be selectively sampled and read into the memory of DSP 50 via selective assertion of the READ ENABLE connection to flash ADC 62. As discussed in more detail below, DSP 50 may analyze the output response to identify frequency changes and/or amplitude phenomena indicating that mass has dislodged from a transducer and/or that a rupture event has occurred.

Figure 3:
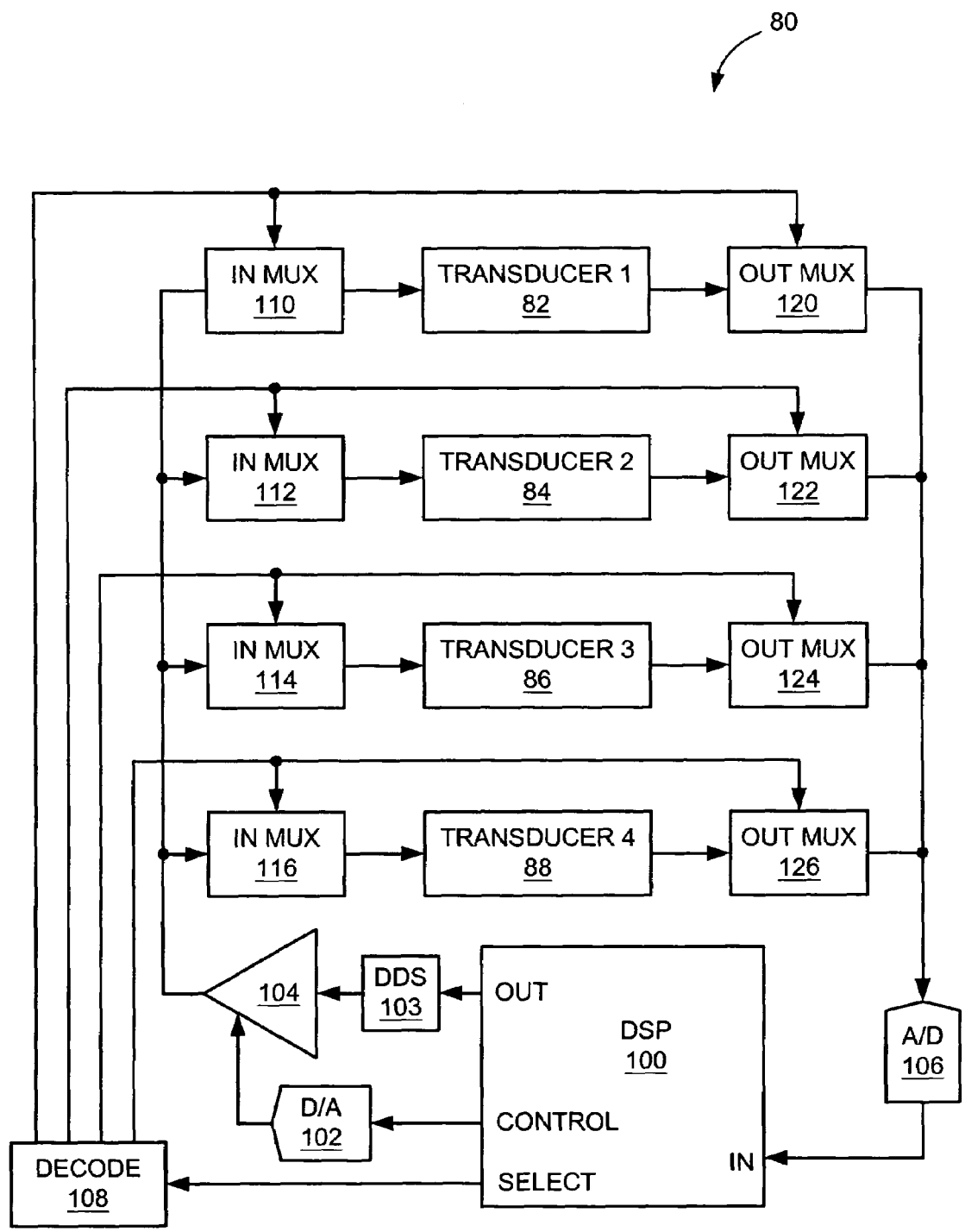
FIG. 3 is a schematic depiction of another embodiment of a transducer-based sensor system according to the present description.

FIG. 3 depicts another transducer system 80. Instead of single-port transducers, system 80 includes an array of two-port transducers 82, 84, 86 and 88. As in the previous example, a controller may be provided to drive and process output from the array. Specifically, system 80 includes a DSP 100 configured to drive the transducers with drive signals applied via the combined operation of DSP 100, DAC 102 and amplifier 104. The resulting output is read into DSP 100 via ADC 106. Transducers within the array may be selected via operation of decode section 108, input multiplexer sections 110, 112, 114 and 116 and output multiplexer sections 120, 122, 124 and 126.

A variety of different drive signals may be employed with the present systems and methods to produce oscillations or other transducer movement, for example to produce forces to induce dislodgment of material (e.g., a rupture event in which antibody-antigen bond(s) break). In many cases, it will be desirable to drive the transducers with a drive signal having a voltage waveform with multiple frequency components. This is in contrast with conventional rupture event systems, in which only pure sinusoidal drive signals are employed. Such signals have only one primary frequency component, and other frequencies are only negligibly present, if at all.

The following co-pending U.S. patent applications provide further examples of transducer-based systems and methods that may be employed in connection with the systems and methods described herein: U.S. patent application Ser. No. 10/286,071 "Transducer-Based Sensor System with Multiple Drive Signal Variants" by Daniel R. Blakley, filed Oct. 31, 2002; U.S. patent application Ser. No. 10/355,396 "Transducer-Based Sensor System" by Daniel R. Blakley, filed Jan. 31, 2003; U.S. patent application Ser. No. 10/356,084 "Sensor System and Method Employing Shared Transducer Elements" by Daniel R. Blakley, filed Jan. 31, 2003; and U.S. patent application Ser. No. 10/632,290 "Multiple-Transducer Sensor System and Method With Selective Activation and Isolation of Individual Transducers" by Daniel R. Blakley, filed Jul. 31, 2003. The disclosures of these patent applications are incorporated herein by this reference, in their entireties and for all purposes.

Figure 4A:
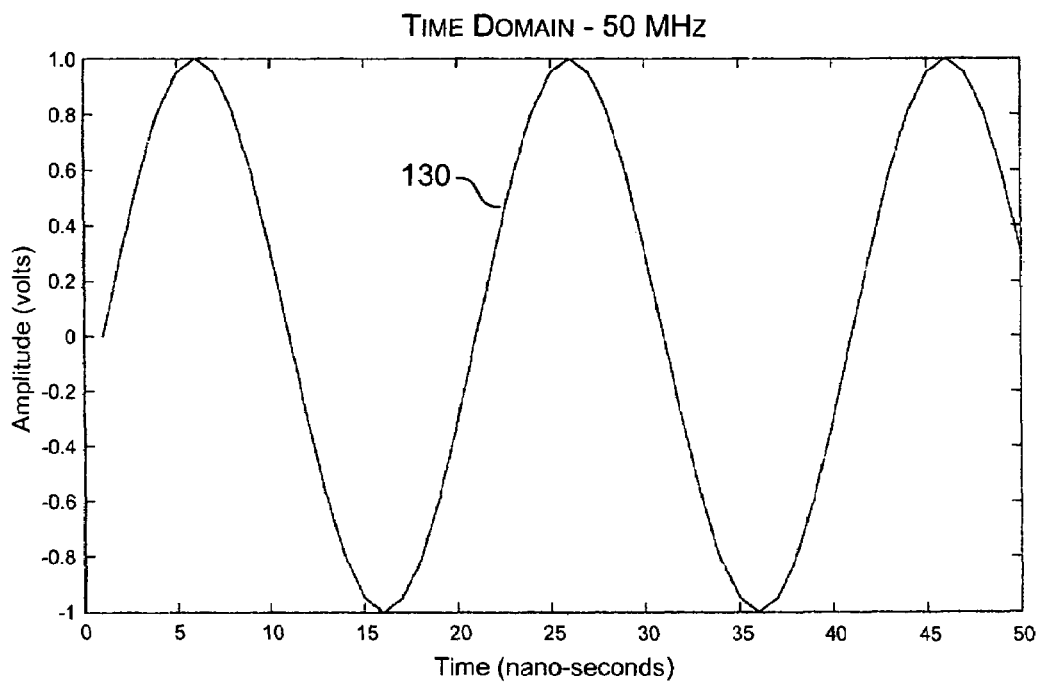
FIGS. 4A and 4B are time domain and frequency domain representations, respectively, of an embodiment of an exemplary single-frequency drive signal that may be employed in connection with the systems and methods of the present description.
Figure 4B:
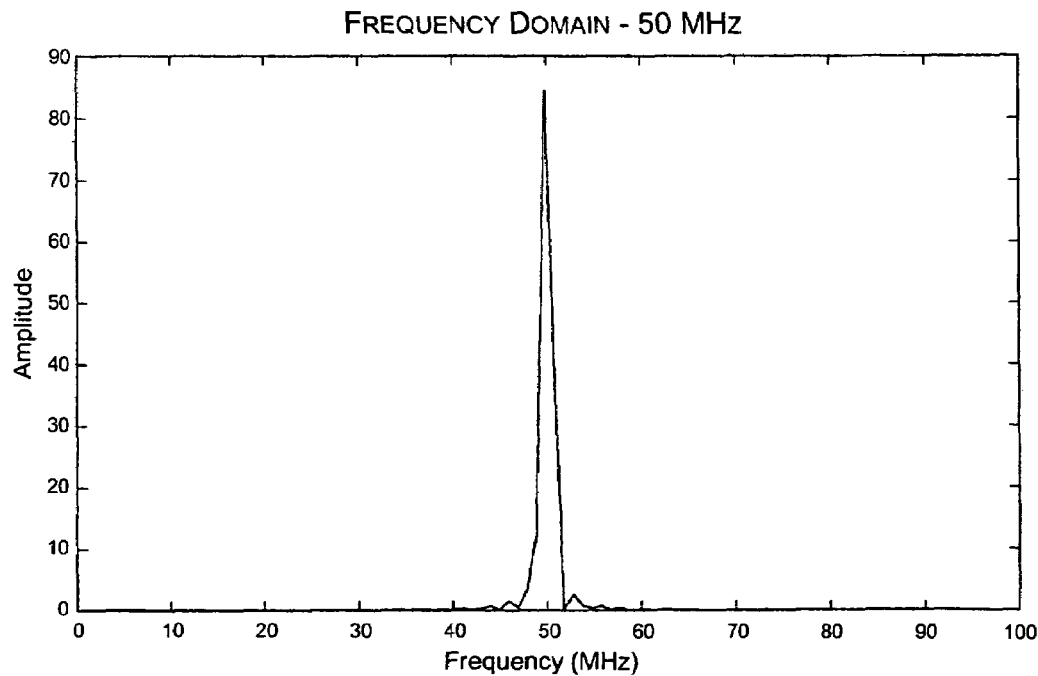

FIGS. 4A, 4B, 5A, 5B, 6A, 6B, 7A and 7B show time domain and frequency domain representations of various exemplary drive signals that may be employed with the systems and devices described herein. FIGS. 4A and 4B show time domain and frequency domain representations, respectively, of a pure sinusoidal drive signal waveform 130, as conventionally employed in prior rupture event systems and methods. As shown in FIG. 4B, the pure sinusoidal signal has only one frequency component. In existing RES systems, the pure sinusoidal signal is applied at a particular amplitude and frequency, and the resulting transducer response is examined to determine if a rupture event occurred, such as breaking of a bond. If no event is detected, the signal amplitude is increased (e.g., to produce greater acceleration and thus a greater force to induce bond breakage), the resulting response is analyzed, and so on until an event is detected.

The process of repetitively increasing amplitude and searching for a response can be fairly time consuming, particularly in a large array of transducers. As discussed above, rupture events and other mass dislodgments are detected through changes in resonant behavior of the transducer. To identify changes in resonance, prior systems repeatedly and frequently sweep through a range of frequencies to determine what the resonant frequency is and/or whether the transducer is currently being driven at resonance. Use of a drive signal with only one frequency component, such as a pure sinusoid, may require resonance determinations to be performed more frequently.

The resonance determination for a given transducer typically is performed by decreasing the amplitude of the sinusoidal drive signal to a magnitude where it will not cause any dislodgment (e.g., a rupture event). The low amplitude signal is then swept through the range of potential frequencies, and the resulting physical response of the transducer is observed by analyzing the electrical output of the transducer. The frequency at which the maximum movement is observed is determined to be the resonant frequency. The determined resonant frequency is then compared to recent values to determine what, if any, change has occurred, and the magnitude of the change. The drive signal amplitude may then be increased once again to the desired operational level (e.g., the level used to induce bond breakage) and the transducer is again accelerated as described above.

Figure 5A:
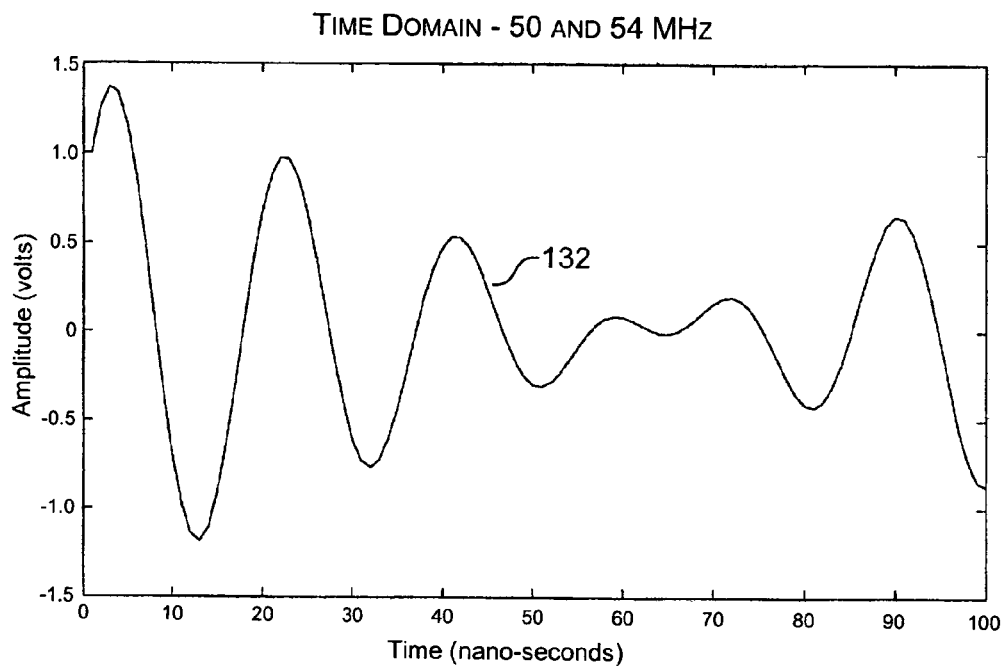
FIGS. 5A and 5B are time domain and frequency domain representations, respectively, of an embodiment of an exemplary multiple-frequency drive signal that may be employed in connection with the systems and methods of the present description.
Figure 5B:
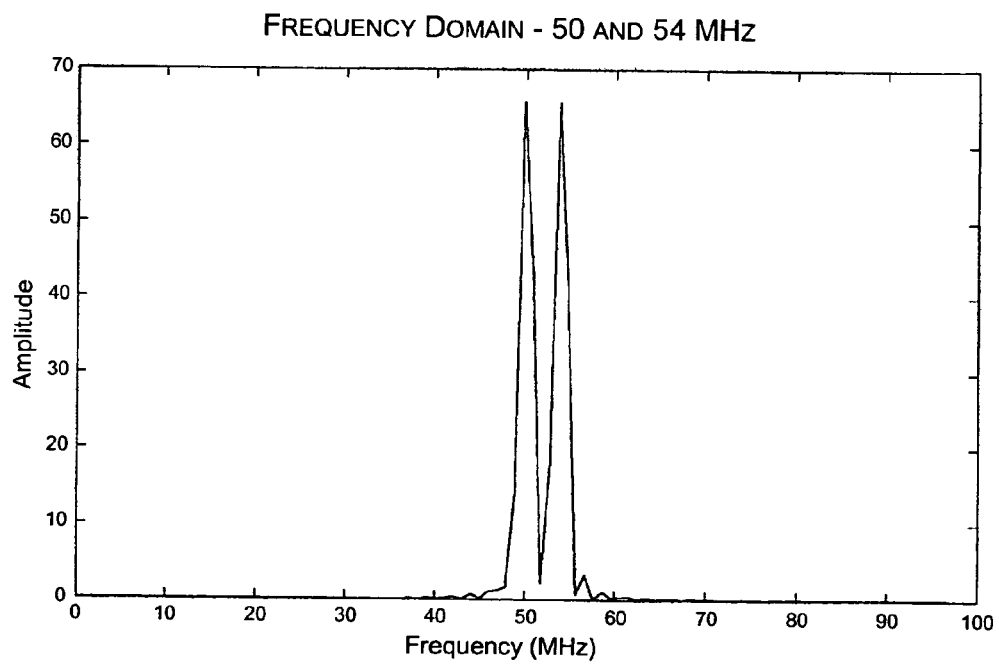
Figure 6A:
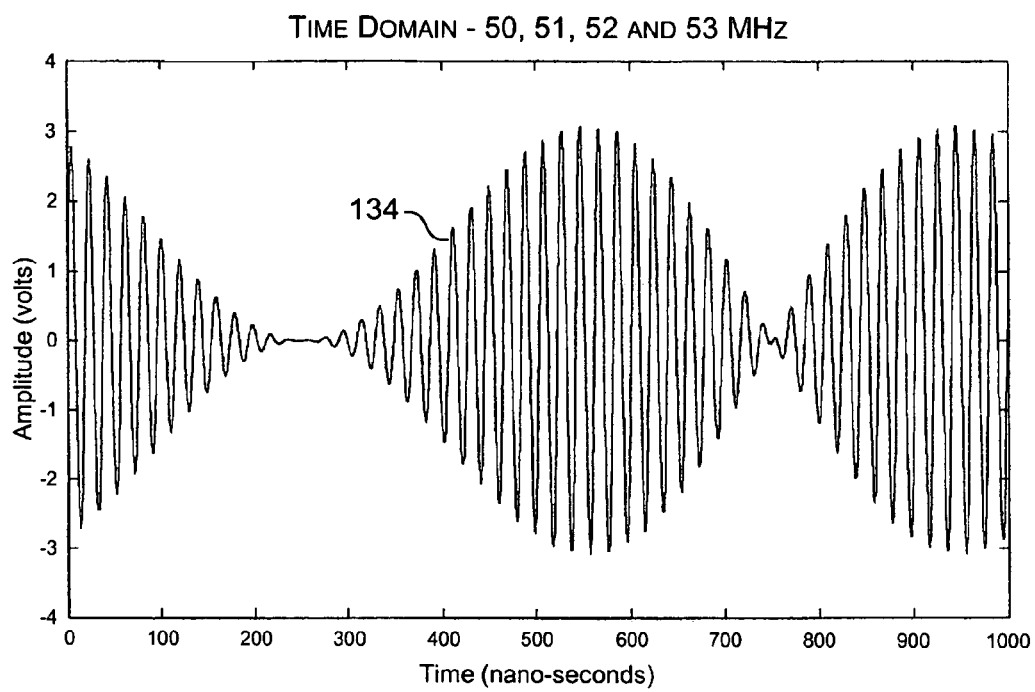
FIGS. 6A and 6B are time domain and frequency domain representations, respectively, of an embodiment of another exemplary multiple-frequency drive signal that may be employed in connection with the systems and methods of the present description.
Figure 6B:
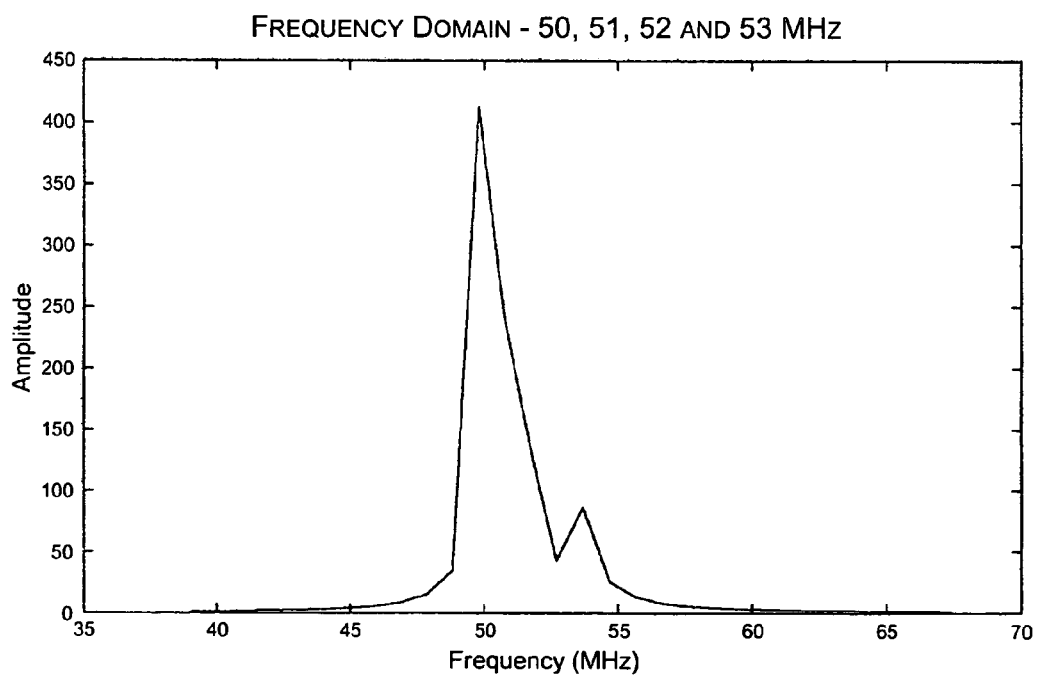
Figure 7A:
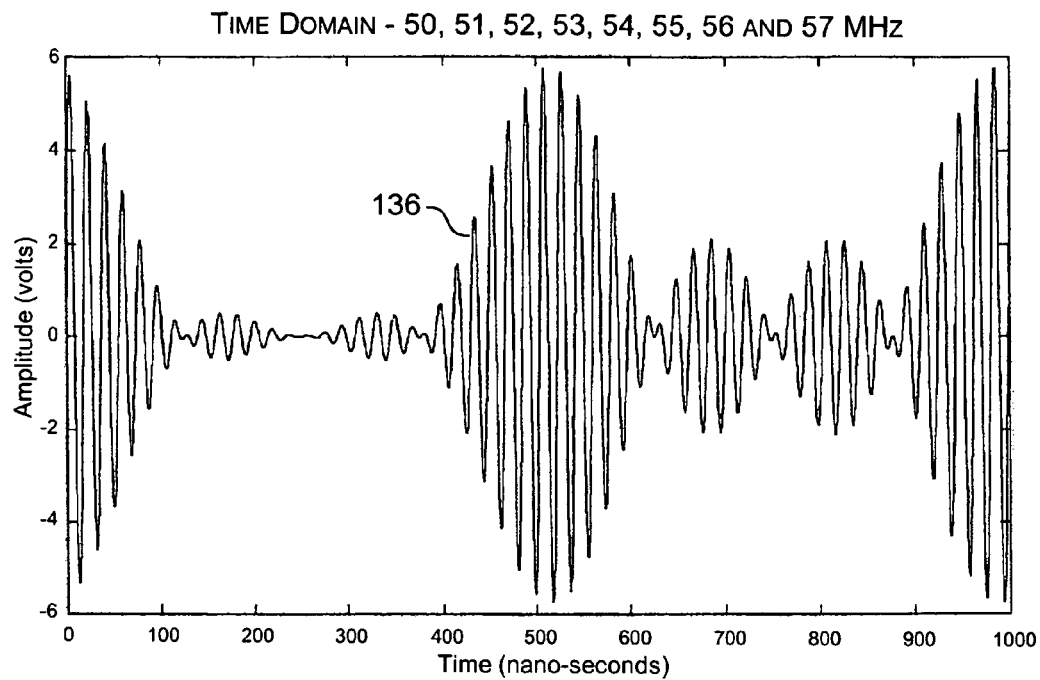
FIGS. 7A and 7B are time domain and frequency domain representations, respectively, of an embodiment of another exemplary multiple-frequency drive signal that may be employed in connection with the systems and methods of the present description.
Figure 7B:
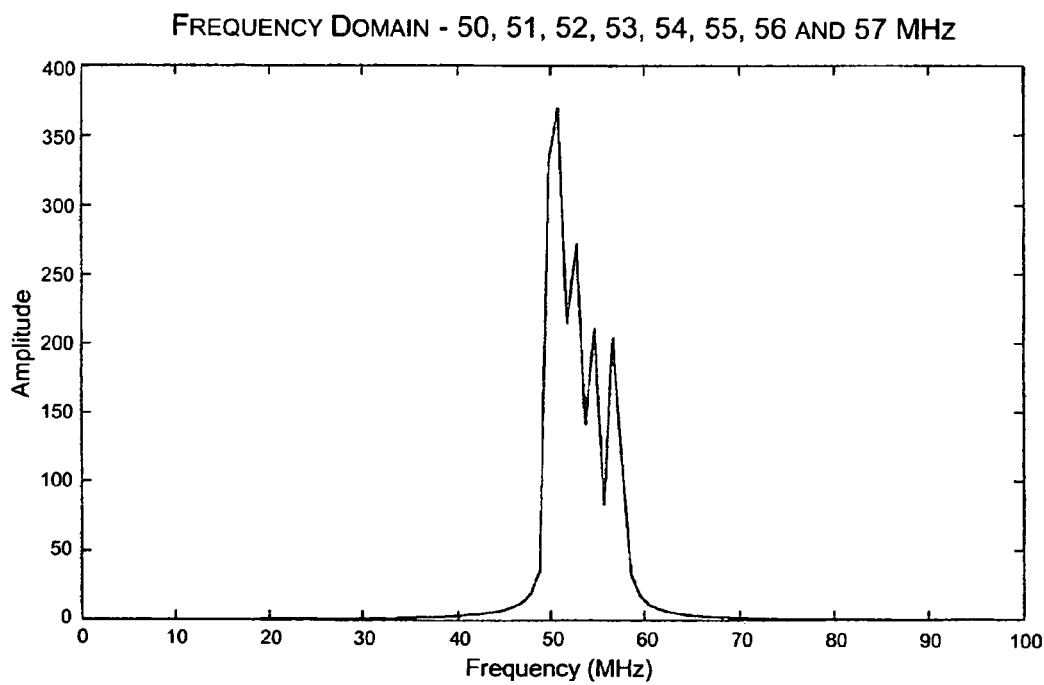

FIGS. 5A, 5B, 6A, 6B, 7A and 7B show time domain and frequency domain representations of alternate drive signal waveforms having multiple frequencies. Specifically, FIGS. 5A and 5B are time domain and frequency domain representations, respectively, of a drive signal waveform 132 having components at 50 and 54 MHz. FIGS. 6A and 6B are time domain and frequency domain representations, respectively, of a drive signal waveform 134 having components at 50, 51, 52 and 53 MHz. FIGS. 7A and 7B are time domain and frequency domain representations, respectively, of a drive signal waveform 136 having components at 50, 51, 52, 53, 54, 55, 56 and 57 MHz. In these examples, the drive signal may be formed by combining sinusoids (e.g., sine and/or cosine waves) at the respective frequencies using suitable amplitude coefficients.

It should be appreciated that FIGS. 5A, 5B, 6A, 6B, 7A and 7B show illustrative examples only, and many other multiple-frequency waveforms may be employed. For example, the frequencies in these waveforms are intended to be illustrative only, and it should be understood that transducer devices may be operated at much higher oscillatory frequencies in rupture event scanning and other applications.

Furthermore, in selecting frequency components for a given waveform, the Q factor of the transducers within the system will often be a consideration in determining the selection of frequencies within a given waveform. For example, it may be desirable to have numerous closely-spaced frequencies in a drive signal waveform used to drive a transducer device with a relatively high Q factor. In high Q devices, even a very small mass dislodgment could place the transducer off resonance relative to a frequency component within the waveform. If the next highest frequency component within the signal had a frequency that was too much higher than the first frequency, then the device could fall "between" the two frequencies, such that neither frequency component could produce a resonant response, due to the relatively high Q factor of the transducer. Accordingly, frequency components for the drive signal waveforms of the present description may be selected based upon transducer Q factors, and/or upon the expected mass dislodgments to occur during operation.

Figure 8:
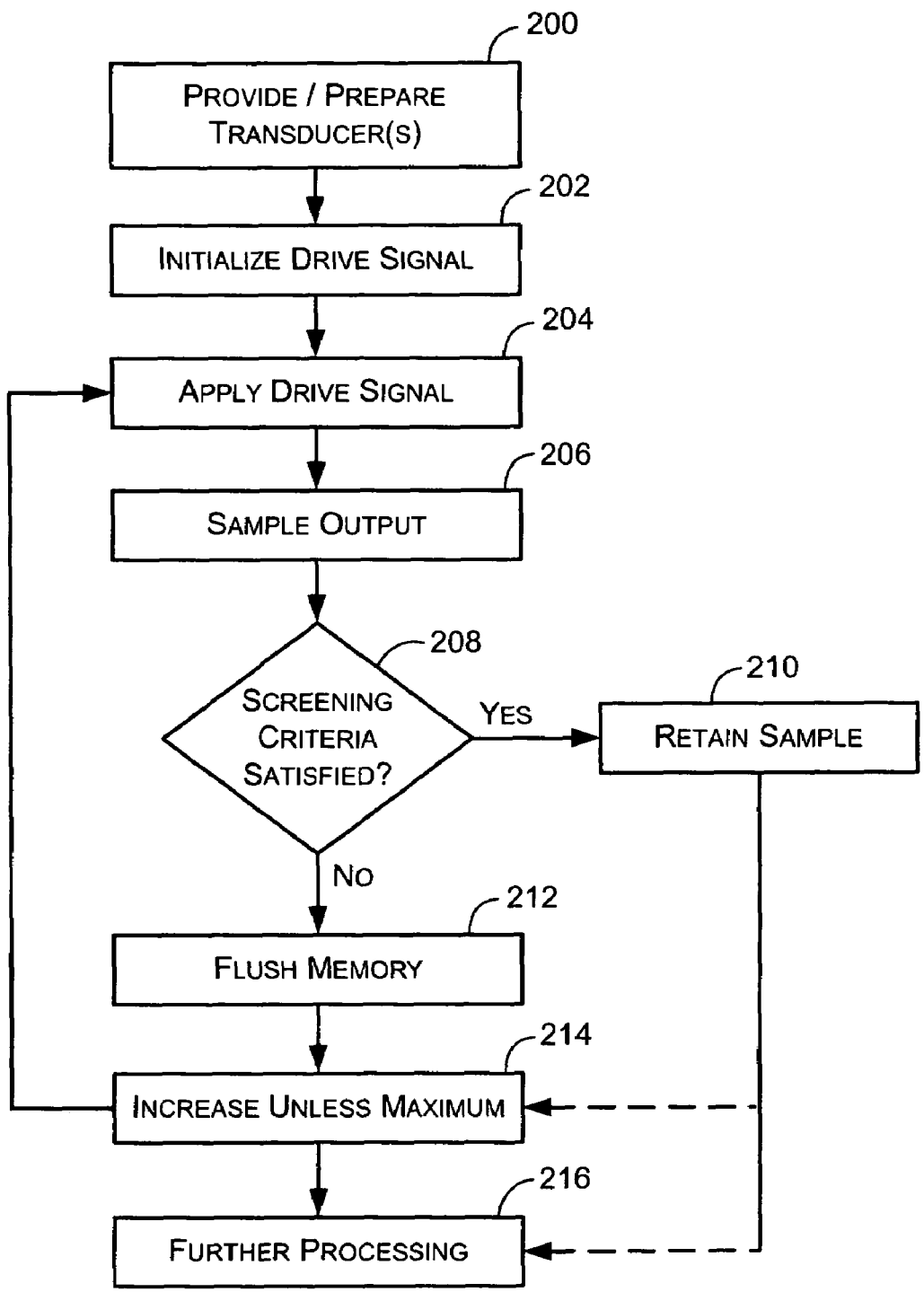
FIGS. 8 and 9 depict exemplary implementations of methods of using an embodiment of a transducer-based system to perform detection and/or sensing operations on a sample material.
Figure 9:
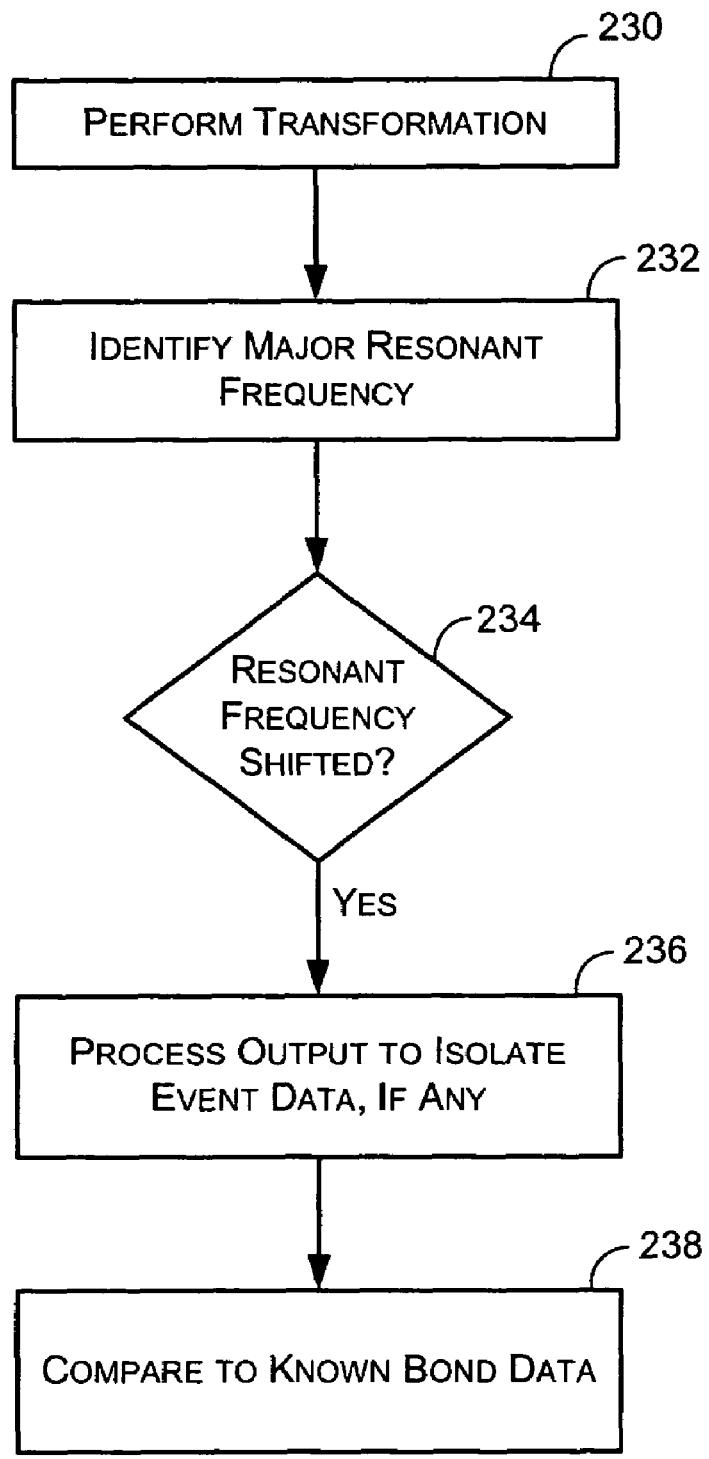

FIGS. 8 and 9 depict exemplary methods for driving a transducer or transducer array, and analyzing the resulting output. The methods of the present description commonly employ multiple-frequency drive signals, as in the examples of FIGS. 5A, 5B, 6A, 6B, 7A and 7B, and may be implemented in connection with or independently of the embodiments discussed above.

Referring first to FIG. 8, a transducer or array of transducers is provided at 200, and the transducers are prepared for excitation with a drive signal. In particular, the transducers may be provided with an immobilized binding partner material and a sample material, as described above with reference to FIGS. 1–3. The sample material and binding partner material typically are brought into close contact to facilitate bond formation between constituent components of the materials (e.g., between an antibody in immobilized binding partner material 22 and an antigen in sample material 24). In some implementations, a spraying device may be employed in connection with systems 40 or 80 to spray the sample material onto a surface of the transducer to which the immobilized binding partner material has been applied. Alternatively, the transducers may be prepared with a binding partner material and sample material in advance. The preparation process may also include applying an initialization drive signal to the transducers in order to move the transducers and thereby facilitate formation of bonds between the sample material and immobilized binding partner material.

As shown at 202, the method may further include initializing the drive signal that is to be used to accelerate the transducer(s). As indicated above, it will often be desirable to employ drive signals having waveforms with multiple frequency components. Accordingly, drive signal initialization may include determining the specific frequency components that are to be present in the drive signal, based on the expected resonance behavior of the transducer. This may involve, for example, determining the initial resonant frequency of the prepared transducer (e.g., a transducer with a binding partner and sample material disposed thereon). Referring to FIG. 3, DSP 100, DAC 102 and amplifier 104 may be used to apply initial drive signals to transducers 82, 84, 86 and 88 in order to identify the initial resonant frequencies of the transducers (e.g., prior to any rupture events or other dislodgment of mass from the transducers).

The initial resonant frequency of a transducer may be used to establish a lower bound for the frequencies to be used in the drive signal, as the resonant frequency will increase as mass dislodges from the transducer. Other frequencies may be selected based on the particular sample material. For example, for a given sample, it may be relatively easy to estimate how much mass will break away during oscillation of the transducer (e.g., due to bonds breaking). This may be used to establish an upper bound for frequency components in the drive signal. These and other considerations, such as the Q factor of the transducers (see above discussion), may dictate how signal components with intermediate frequencies are incorporated into the drive signal.

In any event, it should be understood that use of a multiple-frequency drive signal may produce a resonant response even in the face of changes in the effective mass of the transducer. A pure sinusoid (a single frequency drive signal), in contrast, will produce a resonant response only if the drive signal is close in frequency to the resonant frequency of the transducer, which of course will change as mass is dislodged. The multiple-frequency drive signal described herein accommodates changes in transducer effective mass and the attendant resonant frequency changes, reducing the need to frequently and repeatedly apply low-amplitude signals to obtain resonance. Also, by reducing the number of low-amplitude scans needed to obtain resonance, overall analysis times are reduced.

Initialization may also involve setting a range of energies to which the prepared transducer will be subjected, and initially setting the drive signal to the lowest energy level (e.g., a minimum amplitude and/or duration for the applied waveform) in the determined range. The range of energy levels to be applied may be determined depending on the particular test to be conducted, and/or on the expected properties of the sample material. For example, system 40 or system 80 may be used to determine whether a sample material contains a particular antigen or pathogen. The immobilized binding partner material would be prepared to contain antibodies corresponding to the antigen/pathogen of interest. Using known bond forces for bonds formed between the particular antibody and antigen, a range of energy levels for the input drive signal may be selected. The range may be selected so that, at some level within the range, the antigen of interest, if present, would rupture away from the immobilized binding partner material due to the shear forces generated through oscillation of the transducer.

It should be understood that the frequency components and energy levels for the drive signal may be determined in advance or dynamically while an experiment or other operation is being conducted. Also, referring to FIGS. 2 and 3, the various components of systems 40 and 80 may be programmed or otherwise configured to carry out the initialization tasks described above and with reference to step 202 in FIG. 8. Typically, once the drive signal parameters have been determined and the drive signal is otherwise initialized, the drive signal is generated for application to the transducers. In the example of FIG. 2, the drive signal waveform is generated by DSP 50 with assistance of DDS 52, DAC 54 and amplifier 56. In FIG. 3, DSP 100 may be used to generate the waveform, with assistance of DAC 102, DDS 103 and amplifier 104.

Still referring to FIG. 8, the method further includes, at 204 and 206, applying the drive signal to the transducer and then sampling the resulting output. Referring to FIG. 2, the drive signal waveform may be generated by DSP 50 and DDS 52, with the signal amplitude being controlled by DSP 50, DAC 54 and amplifier 56. As discussed above, the drive signal may be applied to the selected transducer via RF hybrid device 58. The resulting output from the transducer may be sampled and at least temporarily stored in the memory of DSP 50. In the depicted example, DSP 50 selectively asserts the READ ENABLE input of flash ADC 62 to cause output samples to be read from the selected transducer through RF hybrid device 58 into the DSP's memory through amplifier 60 and flash ADC 62. In the example of FIG. 3, DSP 100 generates the drive signal waveform in conjunction with DDS 103, and the amplitude may be controlled by DSP 100 in cooperation with DAC 102 and amplifier 104. Output samples from the selected transducer are read into DSP 100 through ADC 106.

As shown at 208, the output sample may be screened, for example to determine whether a detailed analysis of the particular sample is desirable. In certain embodiments, for example, output samples may be screened for amplitude phenomena indicating or suggesting that a rupture event has occurred, such as the breaking of a bond(s) formed between an antibody-antigen pair. Because bond forces are often relatively high, when the bonds break they typically produce an acoustic event that is detected by the transducer and manifested in the transducer output sample as a short duration, high amplitude burst.

The amplitude burst typically is at substantially different frequencies than the resonant response attributable to the drive signal that is applied to excite the transducer, and thus may be differentiated from the drive signal by its frequency and amplitude. Although the amplitude associated with the rupture may not be much higher than any noise, crosstalk, or other components present in the output sample, it typically occurs synchronously with the drive signal and this may be extracted synchronously and compared afterward with an amplitude trigger or level threshold. Accordingly, a threshold value may be established, and the output sample may be screened for components having amplitudes higher than the threshold. The threshold may be determined in advance, or calculated during operation based on various parameters. For example, the particular threshold may be determined with reference to amplitudes of certain frequency components present in the drive signal. In addition to or instead of amplitude thresholds, other criteria may be employed to identify output samples of potential interest. For example, the method may include a preliminary analysis for phenomena indicating that a shift in resonant frequency has occurred. An upward shift in resonant frequency would indicate that a mass dislodgment, and thus a potential rupture event, had occurred. The particular output sample could then be retained and analyzed in more detail to determine whether a rupture event had in fact occurred as a result of the transducer excitation.

It should be appreciated that the amplitude phenomena and frequency shifts described above may be considered "rupture indicators," because the presence of these indicators suggests that a rupture event may have occurred. Accordingly, step 208 may be thought of as a preliminary screening analysis in which an output sample is scanned for the presence of rupture indicators. The presence of a rupture indicator typically is not a conclusive indication that an event of interest has occurred, as will be explained below. However, screening for rupture indicators will provide, in many settings, an efficient way to identify output samples of potential interest. Typically, the screening process is substantially faster than the more detailed processing that is required to confirm or deny that an event of interest occurred due to excitation of the transducer.

In any event, the method may include taking different actions depending on whether the screening criteria at step 208 is or is not satisfied. If the criteria is satisfied, for example if the output sample includes components exceeding an established amplitude threshold, then the output sample may be retained, as indicated at 210. Alternatively, as shown at 212, if the screening criteria is not satisfied, then the respective memory location (e.g., within DSP 50 or DSP 100) may be flushed to free up memory resources.

It will at times be desirable to increase the acceleration of the transducer(s), and thus the forces applied to induce bond breakage at the surface of the transducer(s). Typically, these forces are proportional to the energy imparted by the drive signal applied to the transducer. As discussed above, the energy of a given waveform may be viewed in terms of the area under a time domain representation of the waveform. Accordingly, the energy level may be increased by increasing the amplitude and/or duration of the overall waveform, or of certain components of the waveform. For example, the amplitude of a selected frequency component, or of the overall waveform, may be increased. In the depicted exemplary method, the drive signal energy level may be increased at 214 unless the maximum energy level has been reached.

From the above, it should be appreciated that the method may include providing the drive signal to the transducer at successively increasing energy levels. For each energy level, the corresponding output response may be sampled (e.g., at 206). After cycling through all the energy levels, further processing may be performed, as shown at 216. The further processing may include a more thorough analysis of the sampled data, as explained in more detail below. Instead of cycling through the entire range of energies for the applied drive signal, the further processing may be performed as soon as a potential event has been identified, as shown at 210 and 216.

An exemplary method of carrying out additional processing of the output sample(s) is depicted in FIG. 9. As shown at 230, the method may include performing a frequency domain transformation on the output sample. Any practicable transformation technique may be employed, including Fourier, FFT, Hartley, Wavelet or Bracewell transformations. Typically, the transformation yields data that may be analyzed within the frequency domain in terms of amplitude as a function of frequency. As shown at 232, the transformation data may be analyzed to identify the major resonant frequency present in the sampled transducer response.

The method may include, at 234, determination of whether the resonant frequency of the transducer has shifted, for example from prior recorded values. As discussed above, such a shift typically occurs when the effective mass of the transducer changes (e.g., when mass breaks off of the surface of the transducer). Specifically, a decrease in mass produces an increase in resonant frequency.

It should be appreciated that a shift in frequency is not a conclusive indication that an event of interest has occurred. In other words, not all mass dislodgments will have experimental significance. A given experiment might involve determining whether a sample material contains a certain pathogen, such as a particular variety of the streptococcus virus. In such an experiment, the only shift in frequency of interest would be a shift associated with a rupture (e.g., bond breakage) between that variety of streptococcus virus and the immobilized binding partner affixed to the transducer. The sample material may include components other than the antigen of interest (proteins, for example) that become affixed to the transducer. When these proteins break off due to oscillation of the transducer, the resonant frequency will shift, however this shift in frequency is not associated with breakage of the particular antibody-antigen bond that is the subject of the experiment.

Accordingly, as indicated at 236 and 238, once a resonant frequency shift has been detected, the transformation data may be further processed to isolate potential event data, if any is present, and then compare the isolated potential event data to stored values. During isolation, data associated with the transducer's response to the drive signal typically will be subtracted or otherwise removed. Also, various methods may be employed to remove noise and crosstalk from the sample. Isolation may involve deconvolution or other methods, as suitable and appropriate to a given setting. Separation of potential event data is often facilitated by the fact that event data typically occurs at frequencies other than the resonant frequency of the transducer. Accordingly, filtering and like techniques may also be applied in many cases to extract the data that is potentially of interest.

In any case, once the potential event data is isolated, the potential event data may be compared to known values, as shown at 238. For example, data associated with known bonds may be stored within the memories of DSP 50 or DSP 100. Such data might include, for example, data pertaining to the acoustic signatures for a variety of antibody-antigen pairs. In the above example, the known data would include the unique acoustic signature associated with rupture of the streptococcus strain away from partner components (e.g., antigens) within the immobilized binding partner material. Accordingly, at step 238, the isolated potential event data would be compared to the known acoustic signatures, and a match would indicate that the sample material in fact contained the streptococcus strain of interest, and that a rupture event occurred involving the strain of interest.

Transformations into the frequency domain and subsequent analysis can be fairly time consuming. In the exemplary method described above, processing speed may be increased by rapidly screening the sampled data to separate potentially relevant data from data which appears to be not relevant. In the specific examples discussed above, the sampled data is preliminarily screened for amplitude and/or frequency phenomena suggesting or indicating that an event of interest occurred. Use of such screening may be employed to avoid performing a fuller and more time-consuming analysis on all of the data sampled from the transducer(s). This is particularly advantageous given that, in many settings, a large majority of transducer excitations will not produce an event of interest or other mass dislodgment.

While the present embodiments and method implementations have been particularly shown and described, those skilled in the art will understand that many variations may be made therein without departing from the spirit and scope defined in the following claims. The description should be understood to include all novel and non-obvious combinations of elements described herein, and claims may be presented in this or a later application to any novel and non-obvious combination of these elements. Where the claims recite "a" or "a first" element or the equivalent thereof, such claims should be understood to include incorporation of one or more such elements, neither requiring nor excluding two or more such elements.

What is claimed is:

1. A method of performing rupture event scanning, comprising:
   providing a transducer with an immobilized binding partner material and a sample material disposed thereon, where the sample material is applied to the immobilized binding partner material so that, if the sample material includes components having sufficient affinity for the immobilized binding partner material, bonds will form between at least some of such components and the immobilized binding partner material;
   accelerating the transducer to induce bond breakage, where such accelerating is performed by applying a drive signal to the transducer, the drive signal including a waveform having multiple frequency components that are pre-selected based on expected resonance behavior of the transducer; and
   analyzing an output response of the transducer in response to application of the drive signal.

2. The method of claim 1, where accelerating the transducer is performed by applying the drive signal to the transducer at successively increasing energy levels.

3. The method of claim 2, further comprising, for each of the energy levels, obtaining a corresponding output response of the transducer in response to application of the drive signal at such energy level.

4. The method of claim 2, where increasing from one of the energy levels to a successive one of the energy levels includes increasing an amplitude of the waveform.

5. The method of claim 2, where increasing from one of the energy levels to a successive one of the energy levels includes increasing a duration of the waveform.

6. The method of claim 2, where increasing from one of the energy levels to a successive one of the energy levels includes increasing an amplitude and a duration of the waveform.

7. The method of claim 1, where analyzing the output response of the transducer includes determining whether the output response exhibits amplitude phenomena indicating breakage of bonds formed between components of the sample material and the immobilized binding partner material.

8. The method of claim 7, where analyzing the output response of the transducer includes determining whether the output response exceeds an amplitude threshold.

9. The method of claim 7, where analyzing the output response of the transducer includes determining whether the output response exceeds an amplitude threshold at a given frequency or frequencies.

10. The method of claim 8, where if the output response exceeds the amplitude threshold, the method further includes determining whether the output response contains a known acoustic signature associated with breakage of a known bond.

11. The method of claim 10, where determining whether the output response contains a known acoustic signature associated with breakage of a known bond includes performing a frequency domain transformation on the output response of the transducer.

12. The method of claim 1, where analyzing the output response of the transducer includes determining whether the output response indicates a change in resonant frequency of the transducer.

13. The method of claim 12, where if the output response indicates a change in resonant frequency of the transducer, the method further includes determining whether the output response contains a known acoustic signature associated with breakage of a known bond.

14. The method of claim 13, where determining whether the output response contains a known acoustic signature associated with breakage of a known bond includes performing a frequency domain transformation on the output response of the transducer.

15. The method of claim 1, where analyzing the output response includes:
    screening the output response for rupture indicators suggestive of a potential rupture event occurring between the immobilized binding partner material and the sample material; and
    performing further processing on the output response only if the output response contains a rupture indicator, where such further processing includes determining whether the output response contains a known acoustic signature associated with a known bond.

16. The method of claim 15, where screening the output response for rupture indicators includes determining whether the output response exhibits amplitude phenomena indicating breakage of bonds formed between the sample material and the immobilized binding partner material.

17. The method of claim 16, where determining whether the output response exhibits amplitude phenomena includes determining whether the output response exceeds an amplitude threshold.

18. The method of claim 15, where screening the output response for rupture indicators includes determining whether the output response indicates a change in resonant frequency of the transducer.

19. The method of claim 1, further comprising applying an initialization drive signal to the transducer to cause an initial acceleration of the transducer and thereby facilitate formation of bonds between the sample material and the immobilized binding partner material.

20. A method of performing rupture event scanning, comprising:
    providing a transducer with an immobilized binding partner material and a sample material disposed thereon;
    mechanically exciting the transducer at different energy levels;
    obtaining an output response of the transducer for each of the different energy levels;
    screening each of the output responses for rupture indicators suggestive of a potential rupture event occurring between the immobilized binding partner material and the sample material; and
    performing further processing on at least one of the output responses after said screening, where such further processing includes determining whether the output response contains a known acoustic signature associated with breakage of a known bond, and where such further processing is performed for the output response only if the output response contains a rupture indicator.

21. The method of claim 20, where screening each of the output responses for rupture indicators includes determining whether the output response exhibit amplitude phenomena indicating breakage of bonds formed between the immobilized binding partner material and the sample material.

22. The method of claim 21, where screening each of the output responses for rupture indicators includes determining whether the output response exceeds an amplitude threshold.

23. The method of claim 20, where screening each of the output responses for rupture indicators includes determining whether the output response indicates a change in resonant frequency of the transducer.

24. The method of claim 20, where mechanically exciting the transducer includes applying a drive signal to the transducer, the drive signal including a waveform having multiple frequency components that are pre-selected based on expected resonance behavior of the transducer.

25. A transducer-based sensor system for detecting whether a sample material contains a particular component, comprising:
   a controller; and
   a transducer operatively coupled with the controller, the transducer being configured to receive an immobilized binding partner material and the sample material on a surface of the transducer, where the sample material is brought into contact with the immobilized binding partner material so as to induce formation of a bond between the immobilized binding partner and the particular component, if the particular component is present within the sample material,
   where the controller is configured to:
      apply a drive signal to the transducer to mechanically excite the transducer and thereby potentially cause bond breakage, the drive signal including a waveform having multiple frequency components that are pre-selected based on expected resonance behavior of the transducer;
      receive an output response of the transducer in response to application of the drive signal; and
      analyze the output response to determine whether application of the drive signal induced bond breakage between the sample material and the immobilized binding partner material.

26. The system of claim 25, where the controller is configured to mechanically excite the transducer at different energy levels and obtain a corresponding output response for the transducer for each of the energy levels.

27. The system of claim 26, where the controller is configured to analyze the output responses for the energy levels by:
   screening the output responses for rupture indicators suggestive of a potential rupture event occurring between the immobilized binding partner material and the sample material; and
   performing further processing on at least one of the output responses after said screening, where such further processing includes determining whether the output response contains an acoustic signature known to be associated with the bond, and where such further processing is performed for the output response only if the output response contains a rupture indicator.

28. The system of claim 27, where the controller is configured to screen the output responses by determining whether any of the output responses exhibit amplitude phenomena indicating breakage of bonds formed between the sample material and the immobilized binding partner material.

29. The system of claim 28, where the controller is configured to determine whether any of the output responses exhibit the amplitude phenomena by determining whether any of the output responses exceed an amplitude threshold.

30. The system of claim 28, where the controller is configured to determine whether any of the output responses exhibit the amplitude phenomena by determining whether any of the output responses exceed an amplitude threshold at a filtered or selected range of frequencies.

31. The system of claim 27, where the controller is configured to screen the output responses by determining whether any of the output responses indicate a change in resonant frequency of the transducer.

32. The system of claim 25, where the controller is configured to mechanically excite the transducer at a plurality of successively increasing energy levels and obtain a corresponding output response for the transducer for each of the energy levels.

33. The system of claim 32, where, to increase from one of the energy levels to a successive one of the enemy levels, the controller is configured to increase an amplitude of the waveform.

34. The system of claim 32, where, to increase from one of the energy levels to a successive one of the energy levels, the controller is configured to increase a duration of the waveform.

35. The system of claim 32, where, to increase from one of the energy levels to a successive one of the energy levels, the controller is configured to increase an amplitude and a duration of the waveform.

36. The system of claim 32, where the controller is configured to analyze the output responses for the energy levels by:
   screening the output responses for rupture indicators suggestive of a potential rupture event occurring between the immobilized binding partner material and the sample material; and
   performing further processing on at least one of the output responses after said screening, where such further processing includes determining whether the output response contains an acoustic signature known to be associated with the bond, and where such further processing is performed for the output response only if the output response contains a rupture indicator.

37. The system of claim 36, where the controller is configured to screen the output responses by determining whether any of the output responses exhibit amplitude phenomena indicating breakage of bonds formed between the sample material and the immobilized binding partner material.

38. The system of claim 37, where the controller is configured to determine whether any of the output responses exhibit the amplitude phenomena by determining whether any of the output responses exceed an amplitude threshold.

39. The system of claim 37, where the controller is configured to determine whether any of the output responses exhibit the amplitude phenomena by determining whether any of the output responses exceed an amplitude threshold at a filtered or selected range of frequencies.

40. The system of claim 36, where the controller is configured to screen the output responses by determining whether any of the output responses indicate a change in resonant frequency of the transducer.

41. A transducer-based sensor system for analyzing a sample material, comprising:
- transducer means for receiving an immobilized binding partner material and the sample material, the sample material being placed into contact with the immobilized binding partner material;
- drive signal means for mechanically exciting the transducer means, the drive signal means being configured to apply a drive signal to the transducer means, the drive signal including a waveform having multiple frequency components that are pre-selected based on expected resonance behavior of the transducer means; and output processing means for determining whether predetermined bonds existed between the sample material and the immobilized binding partner material, where such determination is performed by processing an output response of the transducer means to determine whether such output response contains an acoustic signature associated with breakage of the predetermined bands.

* * * * *